United States Patent
Wadle et al.

(10) Patent No.: US 6,623,746 B1
(45) Date of Patent: Sep. 23, 2003

(54) PIT EMULSIONS, METHODS OF SOFTENING PAPER USING THE SAME, AND PAPER SUBSTRATES TREATED THEREWITH

(75) Inventors: Armin Wadle, Erkrath (DE); Holger Tesmann, Juechen (DE); Guido Baumoeller, Leichlingen (DE); Mark Leonard, Bexley (GB); Laurence Robbe-Tomine, Ozoir-la-Ferriere (FR); Achim Ansmann, Erkrath (DE); Rolf Wachter, Duesseldorf (DE); Viola Hoerner, Duesseldorf (DE); Ute Griesbach, Duesseldorf (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 0 days.

(21) Appl. No.: 09/743,834

(22) PCT Filed: Jul. 7, 1999

(86) PCT No.: PCT/EP99/04780

§ 371 (c)(1),
(2), (4) Date: May 14, 2001

(87) PCT Pub. No.: WO00/04230

PCT Pub. Date: Jan. 27, 2000

(30) Foreign Application Priority Data

Dec. 15, 1998 (GB) .............................. 9827616
Jul. 16, 1998 (GB) .............................. 9815514

(51) Int. Cl.$^7$ ........................ A01N 25/34; A61F 13/00; A61K 9/00
(52) U.S. Cl. ...................... 424/402; 424/443; 424/449; 424/400
(58) Field of Search ................................ 424/443, 402, 424/400, 449

(56) References Cited

U.S. PATENT DOCUMENTS

| | | |
|---|---|---|
| 3,896,807 A | 7/1975 | Buchalter |
| 4,112,167 A * | 9/1978 | Dake et al. ................. 428/153 |
| 4,172,887 A | 10/1979 | Vanlerberghe et al. |

(List continued on next page.)

FOREIGN PATENT DOCUMENTS

| | | |
|---|---|---|
| CA | 1 185 500 | 4/1985 |
| CA | 2101079 | 8/1994 |
| DE | 11 65 574 | 3/1964 |
| DE | 20 24 051 C3 | 12/1971 |
| DE | 37 13 099 C2 | 10/1987 |
| DE | 43 08 794 C1 | 4/1994 |
| DE | 43 23 615 A1 | 1/1995 |
| DE | 44 42 987 A1 | 6/1996 |
| DE | 195 37 001 A1 | 3/1997 |
| DE | 196 02 902 A1 | 7/1997 |
| DE | 196 04 180 C2 | 12/1997 |
| DE | 197 12 033 A1 | 9/1998 |
| EP | WO 95/35411 | * 12/1995 |
| EP | 0 693 471 A1 | 1/1996 |
| EP | 0 694 521 A1 | 1/1996 |
| EP | 0 818 450 A1 | 1/1998 |
| FR | 2 252 840 | 8/1975 |
| FR | 2 511 253 B1 | 2/1983 |
| FR | 2 620 024 B1 | 3/1989 |
| FR | 2 701 266 | 8/1994 |
| GB | 962919 | 7/1964 |
| GB | 1 333 475 | 10/1973 |
| GB | 2 069 333 A | 8/1981 |
| JP | 62/096404 A | 2/1987 |
| WO | WO91/01295 | 2/1991 |
| WO | WO95/01773 | 1/1995 |
| WO | WO95/16824 | 6/1995 |
| WO | WO95/35411 | 12/1995 |
| WO | WO95/35412 | 12/1995 |
| WO | WO97/30216 | 8/1997 |

OTHER PUBLICATIONS

Puchta, et al., Tenside Surf. Det., vol. 30, Carl Hanser Verlag, München, (1993), pp. 186–191.
Brock, Tenside Surf. Det, vol. 30, Carl Hanser Verlag, München, (1993), pp. 394, 396 & 398.
Lagerman, et al., JAOCS, vol 71, (Jan., 1994), pp. 97–99.
Shapiro, et al., Cosmetics & Toiletries, vol. 109, (Dec., 1994), pp. 77, 78 & 80.
Ullmann's Encyclopedia of Industrial Chemistry, 5$^{th}$ Ed., vol. A6, Weinheim, Verlag Chemie, (1986), pp. 231–332.
Gesslein, et al., HAPPI, vol. 27, (Oct., 1990), pp. 57 & 59.
Skaugrud, Drug Cosm. Ind., vol. 148, (May, 1991), pp. 24, 26 & 30.
Onsoyen, et al., Seifen–Öle–Fette–Wachse, vol. 117, (1991), p. 633–637.
Sannan, et al., Makromol. Chem., vol. 177, (1976), pp. 3589–3600.
Tronnier, et al., J. Soc. Cosmetic Chemists, vol. 24, (1973), pp. 281–290.
Graham, et al., J. Pharm. Pharmac., vol. 26, (1974), pp. 531–534.
Lochhead, et al., Cosmetics & Toiletries, vol. 108, (May, 1993), pp. 95–114, 116–124, 127–130 & 132–135.
Finkel, SÖFW–Journal, vol. 122, (Aug., 1996), pp. 543–546 & 548.
"Kosmetische Färbemittel", Farbstoffkommission der Deutschen Forschungsgemeinschaft, Verlag Chemie, Weinheim, (1984), pp. 81–106.

Primary Examiner—Thurman K. Page
Assistant Examiner—Isis Ghali
(74) Attorney, Agent, or Firm—John E. Drach; Aaron R. Ettelman

(57) ABSTRACT

The use of phase inversion temperature emulsions containing a non-aqueous phase of (a) one or more $C_{8-22}$ fatty acid alkyl esters, (b) one or more $C_{8-22}$ fatty alcohols, (c) one or more $C_{8-22}$ alcohol polyglycol ethers, and (d) one or more $C_{8-22}$ fatty acid partial glycerides, and an aqueous phase; as softening formulations for substrates such as papers, nonwovens, tissues and cloths is described.

24 Claims, No Drawings

U.S. PATENT DOCUMENTS

| | | |
|---|---|---|
| 4,765,976 A | 8/1988 | Grollier et al. |
| 4,786,367 A | 11/1988 | Bogart et al. |
| 5,240,562 A | 8/1993 | Phan et al. |
| 5,705,169 A | 1/1998 | Stein et al. |
| 5,718,891 A | 2/1998 | Prat et al. |
| 5,730,960 A | 3/1998 | Stein et al. |
| 5,945,091 A | 8/1999 | Habeck et al. |
| 5,962,663 A | 10/1999 | Wachter et al. |
| 6,037,460 A * | 3/2000 | Schneider et al. ............ 516/27 |
| 6,037,487 A | 3/2000 | Habeck et al. |
| 6,193,960 B1 | 2/2001 | Metzger et al. |

* cited by examiner

PIT EMULSIONS, METHODS OF SOFTENING PAPER USING THE SAME, AND PAPER SUBSTRATES TREATED THEREWITH

BACKGROUND OF THE INVENTION

The generic term "paper" encompasses about 3,000 different types and articles which can differ, sometimes considerably, in their applications and their properties. Their production involves the use of numerous additives among the most important of which are fillers (for example chalk or kaolin) and binders (for example starch). For tissues and hygienic papers, which come into relatively close contact with the human skin, there is a particular need for an agreeable soft feel which is normally given to the paper by careful selection of the fibers and, in particular, by a high percentage of fresh mechanical wood pulp or cellulose. However, in the interests of economic paper manufacture and from the ecological viewpoint, it is desirable to use large amounts of inferior-quality deinked wastepaper. Unfortunately, this means that the softness of the paper is significantly reduced which is troublesome in practice and can even lead to irritation of the skin, particularly with frequent use.

Accordingly, there has been no shortage of attempts in the past to treat tissue papers by impregnation, coating or other surface treatments in such a way that a more agreeable soft feel is achieved. International patent application WO 95/35411 (Procter & Gamble) relates to tissue papers coated with softening formulations which contain 20 to 80% by weight of a water-free emulsifier (mineral oils, fatty acid esters, fatty alcohol ethoxylates, fatty acid ethoxylates, fatty alcohols and mixtures thereof), 5 to 95% by weight of a carrier (fatty alcohols, fatty acids or fatty alcohol ethoxylates containing 12 to 22 carbon atoms in the fatty group) and 1 to 50% by weight of surfactants with an HLB value of preferably 4 to 20. The Examples mentioned in this document all contain petrolatum as emulsifier. International patent application WO 95/35412 discloses similar tissue papers where water-free mixtures of (a) mineral oils, (b) fatty alcohols or fatty acids and (c) fatty alcohol ethoxylates are used as softeners. International patent application WO 95/16824 (Procter & Gamble) describes softening formulations for tissue papers containing mineral oil, fatty alcohol ethoxylates and nonionic surfactants (sorbitan esters, glucamides). In addition, International patent application WO 97/30216 (Kaysersberg) describes softening formulations for paper handkerchiefs which contain (a) 35 to 90% by weight of long-chain fatty alcohols, (b) 1 to 50% by weight of wax esters containing 24 to 48 carbon atoms, (c) 0 to 20% by weight of nonionic emulsifiers and (d) 0 to 50% by weight of mineral oil. From the applicational standpoint, however, the softness and sensorial properties of the treated papers are still in need of improvement.

Accordingly, the problem addressed by the present invention was to provide preparations with which dry utility papers, more particularly tissue papers, and tissue cloths having a particularly agreeable soft feel and excellent skin-care properties could even be produced using raw materials comprising a high percentage of recycled paper. At the same time, only readily biodegradable auxiliaries would be used and the preparations would penetrate easily into the tissue, would be uniformly dispersed therein and, even in highly concentrated form, would have such a low viscosity that they would be easy to process. In addition, there was a need for preparations with which utility papers, particularly tissue papers, but also tissue cloth with particularly dermatologically compatible properties could be produced. It would also be desirable to provide the utility papers with additional properties such as, for example, anti-inflammatory or anti-microbial properties. In addition, it would be desirable to obtain utility papers that would retain their skin care properties for prolonged periods, particularly in the case of products expected to withstand prolonged storage.

BRIEF SUMMARY OF THE INVENTION

The present invention relates generally to utility and hygenic paper towels (e.g., "wipes") and, more particularly, to the use of emulsions of various fatty compounds produced by phase inversion temperature processes, as impregnating and softening formulations.

The present invention relates to the use of PIT emulsions containing

| (a) | $C_{8-22}$ and preferably $C_{12-18}$ fatty acid alkyl esters, |
| (b) | $C_{8-22}$ and preferably $C_{12-18}$ fatty alcohols, |
| (c) | $C_{8-22}$ and preferably $C_{12-18}$ alcohol polyglycol ethers and |
| (d) | $C_{8-22}$ and preferably $C_{12-18}$ fatty acid partial glycerides | as impregnating and softening formulations for papers, nonwovens and cloths, preferably for treating the skin.

It has surprisingly been found that preparations of the type mentioned above are capable of imparting an agreeable soft feel, even to particularly critical tissue paper comprising up to 95% by weight recycled paper and tissue cloth. The emulsions produced by the phase inversion temperature process have low viscosities, even in highly concentrated form, so that they are easy to process. By virtue of their small droplet size (<100 μm), the emulsions penetrate very quickly into the tissues and are uniformly dispersed therein. Another advantage is that the substantially odorless preparations are ecotoxicologically safe and, in particular, are readily biodegradable.

DETAILED DESCRIPTION OF THE INVENTION

Tissue Papers and Tissue Cloths

Tissue papers to which the present invention relates may have a single-ply or multiple-ply structure. In general, the papers have a weight per square meter of 10 to 65 and preferably 15 to 30 g and a density of 0.6 g/cm³ or lower. Examples of tissue papers to which the use according to the invention is applicable are toilet papers, paper handkerchiefs, facial wipes, make-up removing wipes, freshening wipes, kitchen roll and the like. Depending on the particular application, the tissues may contain special active ingredients, for example moisturizers, insect repellents (after-sun wipes), dihydroxyacetone, deodorizers, surfactants, alcohols (freshening wipes), skin-care oils, anti-inflammatory agents (baby wipes) and the like. Apart from paper-based tissues, the use according to the invention is also applicable to corresponding tissue cloths made of fibers or fleeces.

Fatty Acid Alkyl Esters

Component (a) of the softening formulations may consist of fatty acid alkyl esters corresponding to formula (I):

$$R^1CO-OR^2 \qquad (I)$$

in which R¹CO is a linear or branched, saturated or unsaturated acyl group containing 8 to 22, preferably 12 to 18 and more preferably 14 to 16 carbon atoms and R² is a linear or branched alkyl and/or alkenyl group containing 6 to 22 carbon atoms. Typical examples are the esters of caprylic acid, isononanoic acid, capric acid, lauric acid, myristic acid, palmitic acid, palmitoleic acid, stearic acid, isostearic acid, oleic acid, elaidic acid, petroselic acid, elaeostearic acid, arachic acid, gadoleic acid, behenic acid and erucic acid and technical mixtures thereof with caproic alcohol, caprylic alcohol, 2-ethylhexyl alcohol, capric alcohol, lauryl alcohol, isotridecyl alcohol, myristyl alcohol, cetyl alcohol, palmitoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and technical mixtures thereof. Wax esters, i.e. fatty acid alkyl esters which have a plastic but firm consistency at 20° C. and which contain a total of 24 to 48 carbon atoms, are preferably used. Typical examples are myristyl myristate, cetearyl isononanoate, cetyl palmitate, cetyl stearate, stearyl palmitate, stearyl stearate and the like.

Fatty Alcohols

Fatty alcohols which may be used as component (b) are understood to be primary alcohols which preferably correspond to formula (II):

$$R^3OH \tag{II}$$

in which $R^3$ is a linear or branched alkyl and/or alkenyl group containing 8 to 22, preferably 12 to 18 and more preferably 14 to 16 carbon atoms. Typical examples are caprylic alcohol, capric alcohol, lauryl alcohol, myristyl alcohol, cetyl alcohol, palmitoleyl alcohol, stearyl alcohol, isostearyl alcohol, oleyl alcohol, elaidyl alcohol, petroselinyl alcohol, elaeostearyl alcohol, arachyl alcohol, gadoleyl alcohol, behenyl alcohol, erucyl alcohol and brassidyl alcohol and the technical mixtures thereof obtained, for example, in the high-pressure hydrogenation of technical methyl esters based on fats and oils or aldehydes from Roelen's oxosynthesis and as monomer fraction in the dimerization of unsaturated fatty alcohols. Technical fatty alcohols containing 12 to 18 carbon atoms, for example coconut oil, palm oil, palm kernel oil or tallow fatty alcohol, are preferred. Guerbet alcohols, i.e. primary alcohols branched in the 2-position which may be obtained by base-catalyzed condensation of fatty alcohols containing 8 to 10 carbon atoms, may also be used. Cetyl alcohol, stearyl alcohol, cetearyl alcohol, behenyl alcohol and mixtures thereof or 2-octyl dodecanol are preferably used.

Alcohol Polyglycol Ethers

Alcohol polyglycol ethers which form component (c) are understood to be products of the addition of ethylene and/or propylene oxide onto fatty alcohols of group (b) or oxoalcohols with the same chain length which preferably correspond to formula (III):

$$R^4O(CH_2CHR^5O)_nH \tag{III}$$

in which $R^4$ is a linear or branched alkyl and/or alkenyl group containing 8 to 22, preferably 12 to 18 and more preferably 14 to 16 carbon atoms, $R^5$ is hydrogen or methyl and n is a number of 1 to 50. Typical examples are the adducts of on average 1 to 50, preferably 5 to 40 and more preferably 10 to 20 moles of ethylene oxide with caprylic alcohol, capric alcohol, lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol and brassidyl alcohol and the technical mixtures thereof obtained, for example, in the high-pressure hydrogenation of technical methyl esters based on fats and oils or aldehydes from Roelen's oxosynthesis and as monomer fraction in the dimerization of unsaturated fatty alcohols. Adducts of 10 to 20 moles of ethylene oxide with technical fatty alcohols containing 16 to 18 carbon atoms, for example cetearyl alcohol or tallow fatty alcohol, are preferred.

Partial Glycerides

Component (d) of the formulations consists of partial glycerides corresponding to formula (IV):

$$HOCH_2CH(OH)CH_2OCOR^6 \tag{IV}$$

in which $R^6CO$ is a linear or branched, saturated or unsaturated acyl group containing 8 to 22, preferably 12 to 18 and more preferably 14 to 16 carbon atoms. The partial glycerides, i.e. monoglycerides, diglycerides and technical mixtures thereof, may still contain small amounts of triglycerides from their production. Typical examples are mono- and/or diglycerides based on caprylic acid, capric acid, lauric acid, palmitic acid, palmitoleic acid, stearic acid, isostearic acid, oleic acid, elaidic acid, petroselic acid, elaeostearic acid, arachic acid, gadoleic acid, behenic acid and erucic acid and technical mixtures thereof. Technical palmitic acid glycerides, stearic acid glycerides, isostearic acid glycerides and/or behenic acid glycerides with a monoglyceride content of 50 to 95% by weight and preferably 60 to 90% by weight are preferably used.

PIT Emulsions

In one preferred embodiment of the invention, PIT emulsions containing—based on the active substance content— 30 to 70% by weight of oil components and 70 to 30% by weight of emulsifiers are used as impregnating and softening preparations. In a particularly preferred embodiment, the emulsions contain—again based on the active substance content—

(a) 2 to 70, preferably 30 to 50% by weight of $C_{8-22}$ fatty acid alkyl esters,
(b) 1 to 40, preferably 10 to 20% by weight of $C_{8-22}$ fatty alcohols,
(c) 10 to 40, preferably 20 to 30% by weight of $C_{8-22}$ alcohol polyglycol ethers,
(d) 1 to 40, preferably 10 to 20% by weight of $C_{8-22}$ fatty acid partial glycerides and
(e) 0 to 70, preferably 10 to 50% by weight of auxiliaries and additives, with the proviso that the quantities add up to 100% by weight. The active substance content can be between 0.5 and 80% by weight, depending on the application. With relatively high active substance contents, the flowability of the emulsions decreases dramatically; with relatively low contents, their effectiveness disappears. The emulsions are preferably marketed as concentrates with an active substance content of 10 to 70% by weight which are subsequently diluted to an in-use concentration of 1 to 15% by weight. If desired, the aqueous phase may also contain polyols, preferably up to 15% by weight of glycerol.

Skin-care Oils

In another preferred embodiment of the invention, skin-care oils are used as the auxiliaries and additives which form component (e) Suitable skin-care oils are, for example, Guerbet alcohols based on fatty alcohols containing 6 to 18 and preferably 8 to 10 carbon atoms, esters of linear carboxylic acids with linear $C_{6-22}$ fatty alcohols, esters of linear $C_{6-22}$ fatty acids with branched alcohols, more particularly 2-ethyl hexanol, esters of hydroxycarboxylic acids with linear or branched $C_{6-22}$ fatty alcohols, more particularly dioctyl malate, esters of linear and/or branched fatty acids with polyhydric alcohols (for example propylene glycol, dimer diol or trimer triol) and/or Guerbet alcohols, triglycerides based on $C_{6-10}$ fatty acids, liquid mono-/di-/triglyceride mixtures based on $C_{6-18}$ fatty acids, esters of $C_{6-22}$ fatty alcohols and/or Guerbet alcohols with aromatic carboxylic acids, more particularly benzoic acid, esters of $C_{2-12}$ dicarboxylic acids with linear or branched alcohols containing 1 to 22 carbon atoms or polyols containing 2 to 10 carbon atoms and 2 to 6 hydroxyl groups, vegetable oils, branched primary alcohols, substituted cyclohexanes, linear and branched $C_{6-22}$ fatty alcohol carbonates, Guerbet carbonates, esters of benzoic acid with linear and/or branched $C_{6-22}$ alcohols (for example Finsolv® TN), linear or branched, symmetrical or nonsymmetrical dialkyl ethers containing 6 to 22 carbon atoms per alkyl group, ring opening products of epoxidized fatty acid esters with polyols, silicone oils and/or aliphatic or naphthenic hydrocarbons. The skin-care oils are preferably used in a quantity of 10 to 50% by weight, based on the active substance content of the PIT emulsions. If skin-care oils are present in the emulsions in the stated quantities, the percentage content of component (a) decreases to preferably 2 to 30% by weight. Accordingly, the technical teaching consists in partly replacing the ester oils which make up component (a) with skin-care oils.

Co-emulsifiers

If desired, the formulations to be used in accordance with the invention may contain other emulsifiers, preferably nonionic, cationic or amphoteric emulsifiers, such as:

(1) $C_{12/18}$ fatty acid monoesters and diesters of addition products of 1 to 30 moles of ethylene oxide with glycerol;
(2) glycerol mono/diesters, sorbitan mono/diesters and sugar mono/diesters of saturated and unsaturated fatty acids containing 6 to 22 carbon atoms or hydroxycarboxylic acids containing 2 to 6 carbon atoms, for example citric acid, malic acid or tartaric acid, and ethylene oxide addition products thereof;
(3) alkyl mono- and oligoglycosides containing 8 to 22 carbon atoms in the alkyl group and ethoxylated analogs thereof;
(4) addition products of 15 to 60 moles of ethylene oxide with castor oil and/or hydrogenated castor oil;
(5) polyol esters and, in particular, polyglycerol esters such as, for example, polyglycerol polyricinoleate, polyglycerol poly-12-hydroxy-stearate or polyglycerol dimerate. Mixtures of compounds from several of these classes are also suitable;
(6) addition products of 2 to 15 moles of ethylene oxide with castor oil and/or hydrogenated castor oil;
(7) partial esters based on linear, branched, unsaturated or saturated $C_{6/22}$ fatty acids, ricinoleic acid and 12-hydroxystearic acid and glycerol, polyglycerol, pentaerythritol, dipentaerythritol, sugar alcohols (for example sorbitol), alkyl glucosides (for example methyl glucoside, butyl glucoside, lauryl glucoside) and polyglucosides (for example cellulose);
(8) mono-, di and trialkyl phosphates and mono-, di- and/or tri-PEG-alkyl phosphates and salts thereof;
(9) wool wax alcohols;
(10) polysiloxane/polyalkyl polyether copolymers and corresponding derivatives;

-continued

(11) mixed esters of pentaerythritol, fatty acids, citric acid and fatty alcohol according to DE-PS 11 65 574 and/or mixed esters of fatty acids containing 6 to 22 carbon atoms, methyl glucose and polyols, preferably glycerol or polyglycerol, and
(12) polyalkylene glycols.

The addition products of ethylene oxide and/or propylene oxide with glycerol monoesters and diesters and sorbitan monoesters and diesters of fatty acids or with castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of addition products of ethylene oxide with glycerol are known as refatting agents for cosmetic formulations from DE-PS 20 24 051.

$C_{8/18}$ alkyl mono- and oligoglycosides, their production and their use as surfactants are known from the prior-art literature. They are produced in particular by reacting glucose or oligosaccharides with primary alcohols containing 8 to 18 carbon atoms. So far as the glycoside component is concerned, both monoglycosides where a cyclic sugar unit is attached to the fatty alcohol by a glycoside bond and oligomeric glycosides with a degree of oligomerization of preferably up to about 8 are suitable. The degree of oligomerization is a statistical mean value on which a homolog distribution typical of such technical products is based.

Other suitable emulsifiers are zwitterionic surfactants. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one—COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-coco-alkylaminopropionate, cocoacylaminoethyl aminopropionate and $C_{12/18}$ acyl sarcosine. According to the invention, other suitable emulsifiers besides ampholytic surfactants are quaternary emulsifiers, those of the esterquat type, preferably methyl-quaternized difatty acid triethanolamine ester salts, being particularly preferred because they further improve softness. "Esterquats" are generally understood to be quaternized fatty acid triethanolamine ester salts. These are known compounds which can be obtained by the relevant methods of preparative organic chemistry. Reference is made in this connection to International patent application WO 91/01295 (Henkel), according to which triethanolamine is partly esterified with fatty acids in the presence of hypophosphorous acid, air is passed through the reaction mixture and the whole is then quaternized with dimethyl sulfate or ethylene oxide. In addition, German patent DE-C1 4308794 (Henkel) describes a process for the production of solid esterquats in which the quaternization of triethanolamine esters is carried out in the presence of suitable dispersants, preferably fatty alcohols. Overviews on this theme have been published by R. Puchta et al. in Tens. Surf. Det., 30, 186 (1993), by Mr. Brock in Tens. Surf. Det., 30, 394 (1993), by R. Lagermann et al. in J. Am. Oil Chem. Soc., 71, 97 (1994) and by I. Shapiro in Cosm. Toil. 109, 77 (1994). The quaternized fatty acid triethanolamine ester salts correspond to formula (V):

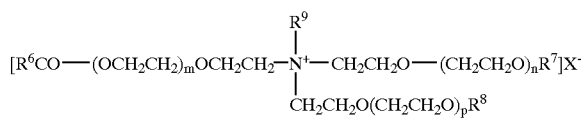

(V)

in which $R^6CO$ is an acyl group containing 6 to 22 carbon atoms, $R^7$ and $R^8$ independently of one another represent hydrogen or have the same meaning as $R^6CO$, $R^9$ is an alkyl group containing 1 to 4 carbon atoms or a $(CH_2CH_2O)_qH$ group, m, n and p together stand for 0 or numbers of 1 to 12, q is a number of 1 to 12 and X is halide, alkyl sulfate or alkyl phosphate. Typical examples of esterquats which may be used in accordance with the present invention are products based on caproic acid, caprylic acid, capric acid, lauric acid, myristic acid, palmitic acid, isostearic acid, stearic acid, oleic acid, elaidic acid, arachic acid, behenic acid and erucic acid and the technical mixtures thereof obtained, for example, in the pressure hydrolysis of natural fats and oils. Technical $C_{12/18}$ cocofatty acids and, in particular, partly hydrogenated $C_{16/18}$ tallow or palm oil fatty acids and $C_{16/18}$ fatty acid cuts rich in elaidic acid are preferably used. To produce the quaternized esters, the fatty acids and the triethanolamine may be used in a molar ratio of 1.1:1 to 3:1. With the performance properties of the esterquats in mind, a ratio of 1.2:1 to 2.2:1 and preferably 1.5:1 to 1.9:1 has proved to be particularly advantageous. The preferred esterquats are technical mixtures of mono-, di- and triesters with an average degree of esterification of 1.5 to 1.9 and are derived from technical $C_{16/18}$ tallow or palm oil fatty acid (iodine value 0 to 40). In performance terms, quaternized fatty acid triethanol-amine ester salts corresponding to formula (V), in which $R^6CO$ is an acyl group containing 16 to 18 carbon atoms, $R^7$ has the same meaning as $R^6CO$, $R^8$ is hydrogen, $R^9$ is a methyl group, m, n and p stand for 0 and X stands for methyl sulfate, have proved to be particularly advantageous. Besides the quaternized fatty acid triethanolamine ester salts, other suitable esterquats are quaternized ester salts of fatty acids with diethanol-alkyamines corresponding to formula (VI):

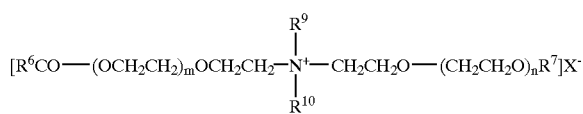

(VI)

in which $R^6CO$ is an acyl group containing 6 to 22 carbon atoms, $R^7$ is hydrogen or has the same meaning as $R^6CO$, $R^9$ and $R^{10}$ independently of one another are alkyl groups containing 1 to 4 carbon atoms, m and n together stand for 0 or numbers of 1 to 12 and X stands for halide, alkyl sulfate or alkyl phosphate. Finally, another group of suitable esterquats are the quaternized ester salts of fatty acids with 1,2-dihydroxypropyl dialkylamines corresponding to formula (VII):

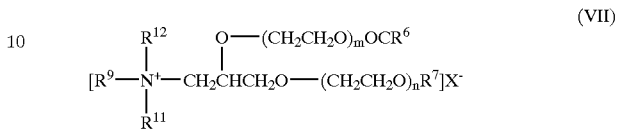

(VII)

in which $R^6CO$ is an acyl group containing 6 to 22 carbon atoms, $R^7$ is hydrogen or has the same meaning as $R^6CO$, $R^9$, $R^{10}$ and $R^{11}$ independently of one another are alkyl groups containing 1 to 4 carbon atoms, m and n together stand for 0 or numbers of 1 to 12 and X stands for halide, alkyl sulfate or alkyl phosphate. So far as the choice of the preferred fatty acids and the optimal degree of esterification are concerned, the examples mentioned for (V) also apply to the esterquats corresponding to formulae (VI) and (VII).

In another embodiment of the invention, the PIT emulsions contain active substances as additives and auxiliaries.

Active Substances—Chitosans

In one particular embodiment of the invention, the PIT emulsions contain chitosans as active sustances (e-1). It has surprisingly been found that, by adding chitosans to the PIT emulsions, the utility papers obtained not only have paticular softness, they are also distinguished by considerably improved dermatological compatibility. More particularly, the film-forming properties of the chitosans have a moisturizing effect and improve the feeling of the emulsion on the skin, particularly in the long term. In addition, the adhesion of other active principles, for example UV filters or perfume oils, is increased. The chitosans also have an antimicrobial effect and thus impart this property to the utility papers treated with these emulsions.

Chitosans are biopolymers which belong to the group of hydrocolloids. Chemically, they are partly deacetylated chitins differing in their molecular weights which contain the following—idealized—monomer unit:

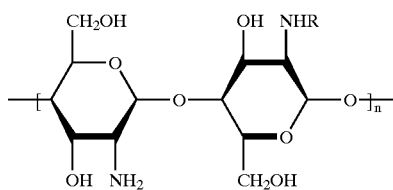

In contrast to most hydrocolloids, which are negatively charged at biological pH values, chitosans are cationic biopolymers under these conditions. The positively charged chitosans are capable of interacting with oppositely charged surfaces and are therefore used in cosmetic hair-care and body-care products and pharmaceutical preparations (cf. Ullmann's Encyclopedia of Industrial Chemistry, 5th Ed., Vol. A6, Weinheim, Verlag Chemie, 1986, pages 231–332). Overviews of this subject have also been published, for example, by B. Gesslein et al. in HAPPI 27, 57 (1990), O. Skaugrud in Drug Cosm. Ind. 148, 24 (1991) and E. Onsoyen et al. in Seifen-Öle-Fette-Wachse 117, 633 (1991). Chitosans are produced from chitin, preferably from the shell residues of crustaceans which are available in large quantities as inexpensive raw materials. In a process described for the first time by Hackmann et al., the chitin is normally first deproteinized by addition of bases, demineralized by addition of mineral acids and, finally, deacetylated by addition of strong bases, the molecular weights being distributed over a broad spectrum. Corresponding processes are known, for example, from Makromol. Chem. 177, 3589 (1976) or French patent application FR-A 2701266. Preferred types are those which are disclosed in German patent applications DE-A1 4442987 and DE-A1 19537001 (Henkel) and which have an average molecular weight of 800,000 to 1,200,000 dalton, a Brookfield viscosity (1% by weight in glycolic acid) below 5,000 mpas, a degree of deacetylation of 80 to 88% and an ash content of less than 0.3% by weight. Besides the chitosans as typical cationic biopolymers, anionically or nonionically derivatized chitosans such as, for example, the carboxylation, succinylation or alkoxylation products described, for example, in German patent DE-C2 3713099 (L'Oréal) and in German patent application DE-A1 19604180 (Henkel) are also suitable for the purposes of the invention. In a preferred embodiment, chitosans with an average molecular weight of 10,000 to 5,000,000 dalton, preferably in the range from 30,000 to 100,000 dalton and more preferably in the range from 800,000 to 1,200,000 are used. The chitosans may be present in the preparations according to the invention in quantities of 0.001 to 2.5% by weight and preferably in quantities of 0.01 to 0.5% by weight, based on the active substance content.

Active Substances—(Deoxy)ribonucleic Acids

In another preferred embodiment, the PIT emulsions contain (deoxy)ribonucleic acids as active substances (e-2). It has surprisingly been found that the utility papers treated with the PIT emulsions containing these active substances have particular inflammation-inhibiting and antioxidative properties. In another embodiment of the invention, the PIT emulsions contain chitosans (e-1) and (deoxy)ribonucleic acids (e-2). It has surprisingly been found that PIT emulsions which provide the utility papers with surprising skin-care properties and at the same time anti-inflammatory properties are obtained by combining chitosans and (deoxy)ribonucleic acids. It is particularly worth mentioning in this regard that these properties are long-lasting.

(Deoxy)ribonucleic acids (DNA, RNA) are understood to be high molecular weight filament-like polynucleotides which are derived from 2'-deoxy-β-D-ribonucleosides or D-ribonucleosides which, in turn, are prepared from equivalent quantities of a nucleobase and the pentose 2-deoxy-D-ribofuranose or D-ribofuranose. The use of nucleic acid as active substances in cosmetics is known. For example, French patent application FR-A1 2511253 describes skin-care and sun protection compositions containing highly polymerized DNA. Published Japanese patent application JP-A2 62/096404 (Kanebo) describes cosmetic compositions containing nucleic acids and diisopropylamine dichloroacetate. French patent FR-B1 2620024 (Soc. d'Etudes Dermatologiques) relates to compositions containing nucleic acid derivatives as radical scavengers. Examples include adenine, guanosine, xanthine, hypoxanthine, uracil and ribonucleic acid. International patent application WO 95/01773 (Boston University) describes a process for stimulating pigment production in which DNA fragments, preferably dinucleotides, are transported in liposomal form into the epidermis. Finally, German patent application DE-A1 4323615 relates to compositions containing nucleic acids and fragments thereof as antiaging and sun protection creams.

The DNA or RNA may contain the purine derivatives adenine and guanine and the pyrimidines cytosine and thymine or uracil as nucleobases. In the nucleic acids, the nucleobases are attached by an N-glycosidic bond to carbon atom 1 of the ribose, so that adenosines, guanosines, cytidines and thimidines are formed in the particular individual case. In the acids, a phosphate group attaches the 5'-hydroxy group of the nucleosides to the 3'-OH group of the following phosphate group by a phosphodiester bridge to form single-stranded DNA or RNA. The DNA is generally double-stranded (formation of hydrogen bridge bonds between the corresponding bases) and the RNA single-stranded. Depending on the treatment of the nucleic acids, the DNA and the RNA may be present both in the form of double strands and/or in the form of single strands. Heterodimers (double strand between DNA and RNA) are also possible. The expression (deoxy)ribonucleic acids in the context of the present invention encompasses both double-stranded and single-stranded (deoxy)ribonucleic acids and also mixtures of single strands and double strands. In view of the considerable length-to-diameter ratio, DNA and RNA molecules show a tendency towards strand breakage even under mechanical stressing, for example during extraction. For this reason, the molecular weight of the nucleic acids can reach $10^3$ to $10^9$ dalton. Concentrated DNA or RNA solutions, which are distinguished by liquid crystalline behavior, are used for the purposes of the invention. (Deoxy)ribonucleic acids which are obtained from marine sources, for example by extraction of fish sperm, and which have a molecular weight of 1,000 to 5,000,000 dalton are preferably used. Single-stranded deoxyribonucleic acids of marine origin with a molecular weight of 1,000 to 1,000,000 dalton and more particularly 1,000 to 5,000,000 dalton are particularly preferred. The (deoxy)ribonucleic acids may be present in the preparations according to the invention in quantities of 0.001 to 2.5% by weight and preferably in quantities of 0.1 to 0.5% by weight, based on the composition.

In one particularly preferred embodiment, the emulsions contain—again based on the active substance content—

(a) 2 to 70, preferably 30 to 50% by weight of $C_{8-22}$ fatty acid alkyl esters,
(b) 1 to 40, preferably 10 to 20% by weight of $C_{8-22}$ fatty alcohols,
(c) 10 to 40, preferably 20 to 30% by weight of $C_{8-22}$ alcohol polyglycol ethers,
(d) 1 to 40, preferably 10 to 20% by weight of $C_{8-22}$ fatty acid partial glycerides and
(e) 0 to 70, preferably 10 to 50% by weight of auxiliaries and additives, these auxiliaries and additives containing (e-1) 0.001 to 2.5, preferably 0.01 to 0.5% by weight of chitosans and optionally (e-2) 0 to 2.5, preferably 0 to 0.5% by weight of (deoxy)ribonuleic acids, with the proviso that the quantities shown add up to 100% by weight.

In another preferred embodiment, the emulsions contain—again based on the active substance content—

(a) 2 to 70, preferably 30 to 50% by weight of $C_{8-22}$ fatty acid alkyl esters,
(b) 1 to 40, preferably 10 to 20% by weight of $C_{8-22}$ fatty alcohols,
(c) 10 to 40, preferably 20 to 30% by weight of $C_{8-22}$ alcohol polyglycol esters,
(d) 1 to 40, preferably 10 to 20% by weight of $C_{8-22}$ fatty acid partial glycerides and -continued (e) 0 to 70, preferably 10 to 50% by weight of auxiliaries and additives, these auxiliaries and additives containing (e-1) 0.001 to 2.5, preferably 0.01 to 0.5% by weight of (deoxy)ribonucleic acids and optionally (e-2) 0 to 2.5, preferably 0 to 0.5% by weight of chitosans, with the proviso that the quantities shown add up to 100% by weight.

Other Active Substances

In another embodiment of the invention, the PIT emulsions contain active substances such as, for example, mild surfactants, skin-care oils, superfatting agents, stabilizers, consistency factors, thickeners, polymers, silicone compounds, biogenic agents, deodorizers, anti-dandruff agents, anti-acne agents, film formers, preservatives, hydrotropes, solubilizers, antioxidants, insect repellents, self-tanning agents, perfume oils, UV filters, dyes and the like.

Typical examples of suitable mild, i.e. dermatologically compatible, surfactants, are fatty alcohol polyglycol ether sulfates, monoglyceride sulfates, mono- and/or dialkylsulfosuccinates, fatty acid isethionates, fatty acid sarcosinates, fatty acid taurides, fatty acid glutamates, ether carboxylic acids, alkyl oligoglucosides, fatty acid glucamides, alkyl amidobetaines and/or protein fatty acid condensates (preferably based on wheat proteins).

Superfatting agents may be selected from such substances as, for example, lecithin, lecithin derivatives, polyol fatty acid esters, mono-glycerides and fatty acid alkanolamides, the fatty acid alkanolamides also serving as foam stabilizers. The consistency factors mainly used are fatty alcohols or hydroxyfatty alcohols containing 12 to 22 and preferably 16 to 18 carbon atoms and also partial glycerides, fatty acids or hydroxyfatty acids. A combination of these substances with alkyl oligoglucosides and/or fatty acid N-methyl glucamides of the same chain length and/or polyglycerol poly-1 2-hydroxystearates is preferably used. Suitable thickeners are, for example, polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates (for example Carbopols® [Goodrich] or Synthalens® [Sigma]), polyacrylamides, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Suitable cationic polymers are, for example, cationic cellulose derivatives such as, for example, the quaternized hydroxyethyl cellulose obtainable from Amerchol under the name of Polymer JR 400®, cationic starch, copolymers of diallyl ammonium salts and acrylamides, quaternized vinyl pyrrolidone/vinyl imidazole polymers such as, for example, Luviquat® (BASF), condensation products of polyglycols and amines, quaternized collagen polypeptides such as, for example, Lauryldimonium Hydroxypropyl Hydrolyzed Collagen (Lamequat® L, Grünau GmbH), quaternized wheat polypeptides, polyethyleneimine, cationic silicone polymers such as, for example, Amidomethicone, copolymers of adipic acid and dimethylamino-hydroxypropyl diethylenetriamine (Cartaretine®, Sandoz AG), copolymers of acrylic acid with dimethyl diallyl ammonium chloride (Merqual® 550, Chemviron), polyaminopolyamides as described, for example, in FR-A 2 252 840 and crosslinked water-soluble polymers thereof, cationic chitin derivatives such as, for example, quaternized chitosan, optionally in microcrystalline distribution, condensation products of dihaloalkyls, for example dibromobutane, with bis-dialkylamines, for example bis-dimethylamino-1,3-propane, cationic guar gum such as, for example, Jaguar®CBS, Jaguar®C-17, Jaguar®C-16 of Celanese, USA, quaternized ammonium salt polymers such as, for example, Mirapol® A-15, Mirapol® AD-1, Mirapol®AZ-1 of Miranol, USA.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/ acrylate copolymers, octylacrylamide/methyl methacrylate/ tert.-butylaminoethyl methacrylate/2-hydroxypropyl methacrylate copolymers, polyvinyl pyrrolidone, vinyl pyrrolidone/vinyl acetate copolymers, vinyl pyrrolidone/ dimethylaminoethyl methacrylate/vinyl caprolactam terpolymers and optionally derivatized cellulose ethers and silicones.

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Typical examples of fats are glycerides while suitable waxes are inter alia beeswax, carnauba wax, candelilla wax, montan wax, paraffin wax or microwaxes, optionally in combination with hydrophilic waxes, for example cetyl stearyl alcohol or partial glycerides. Metal salts of fatty acids such as, for example, magnesium, aluminium and/or zinc stearate or ricinoleate may be used as stabilizers. In the context of the invention, biogenic agents are, for example, tocopherol, tocopherol acetate, tocopherol palmitate, ascorbic acid, carotene, deoxyribonucleic acid, retinol, bisabolol, allantoin, phytantriol, panthenol, AHA acids, amino acids, ceramides, pseudoceramides, essential oils, plant extracts, proteolytic enzymes and vitamin complexes.

Suitable deodorizers are, for example, antiperspirants, such as aluminium chlorhydrates. These antiperspirants are colorless hygroscopic crystals which readily deliquesce in air and which accumulate when aqueous aluminium chloride solutions are concentrated by evaporation. Aluminium chlorhydrate is used for the production of perspiration-inhibiting and deodorizing formulations and probably acts by partially blocking the sweat glands through the precipitation of proteins and/or polysaccharides [cf. J. Soc. Cosm. Chem. 24, 281 (1973)]. For example, an aluminium chlorhydrate which corresponds to the formula $[Al_2(OH)_5Cl] \cdot 2.5H_2O$ and which is particularly preferred for the purposes of the invention is commercially available under the name of Locron® from Hoechst AG of Frankfurt, FRG [cf. J. Pharm. Pharmcol. 26, 531 (1975)]. Besides the chlorhydrates, aluminium hydroxy-lactates and acidic aluminium/zirconium salts may also be used. Other suitable deodorizers are esterase inhibitors, preferably trialkyl citrates, such as trimethyl citrate, tripropyl citrate, triisopropyl citrate, tributyl citrate and, in particular, triethyl citrate (Hydagen® CAT, Henkel KGaA, Düsseldorf, FRG). Esterase inhibitors inhibit enzyme activity and thus reduce odor formation. The free acid is probably released through the cleavage of the citric acid ester, reducing the pH value of the skin to such an extent that the enzymes are inhibited. Other esterase inhibitors are dicarboxylic acids and esters thereof, for example glutaric acid, glutaric acid monoethyl ester, glutaric acid diethyl ester, adipic acid, adipic acid monoethyl ester, adipic acid diethyl ester, malonic acid and malonic acid diethyl ester, hydroxycarboxylic acids and esters thereof, for example citric acid, malic acid, tartaric acid or tartaric acid diethyl ester. Antibacterial agents which influence the germ flora and destroy or inhibit the growth of perspiration-decomposing bacteria, may also be present in stick products. Examples of such antibacterial agents are chitosan, phenoxyethanol and chlorhexidine gluconate. 5-Chloro-2-(2,4-dichlorophenoxy)-yphenol, which is marketed under the name of Irgasan® by Ciba-Geigy of Basel, Switzerland, has also proved to be particularly effective.

Suitable antidandruff agents are climbazol, octopirox and zinc pyrithione. Standard film formers are, for example, chitosan, microcrystalline chitosan, quaternized chitosan, polyvinyl pyrrolidone, vinyl pyrrolidone/vinyl acetate copolymers, polymers of the acrylic acid series, quaternary cellulose derivatives, collagen, hyaluronic acid and salts thereof and similar compounds. Suitable swelling agents for aqueous phases are montmorillonites, clays minerals, Pemulen and alkyl-modified Carbopol types (Goodrich). Other suitable polymers and swelling agents can be found in R. Lochhead's review in Cosm. Toil. 108, 95 (1993).

The PIT emulsions may aditionally contain antioxidants. Typical examples are amino acids (for example glycine, histidine, tyro sine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmole to $\mu$mole/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, Superoxid-Dismutase, zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

In addition, hydrotropes, for example ethanol, isopropyl alcohol or polyols, may be used to improve flow behavior. Suitable polyols preferably contain 2 to 15 carbon atoms and at least two hydroxyl groups. Typical examples are glycerol;

alkylene glycols such as, for example, ethylene glycol, diethylene glycol, propylene glycol, butylene glycol, hexylene glycol and polyethylene glycols with an average molecular weight of 100 to 1000 dalton;

technical oligoglycerol mixtures with a degree of self-condensation of 1.5 to 10 such as, for example, technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, particularly those containing 1 to 8 carbon atoms in the alkyl group, for example methyl and butyl glucoside;

sugar alcohols containing 5 to 12 carbon atoms, for example sorbitol or mannitol, sugars containing 5 to 12 carbon atoms, for example glucose or sucrose;

aminosugars, for example glucamine.

Suitable preservatives are, for example, formaldehyde solution, parabens, pentanediol or sorbic acid and the other classes of compounds listed in Appendix 6, Parts A and B of the Kosmetikverordnung ("Cosmetics Directive"). Suitable insect repellents are N,N-diethyl-m-toluamide, pentane-1,2-diol or Insect Repellent 3535. A suitable self-tanning agent is dihydroxyacetone.

Suitable perfume oils are mixtures of natural and synthetic fragrances. Natural fragrances include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamon, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert.butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, lilial and bourgeonal. Examples of suitable ketones are the ionones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, labolanum oil and lavendin oil. The following are preferably used either individually or in the form of mixtures: bergamot oil, dihydromyrcenol, lilial, lyral, citronellol, phenylethyl alcohol, α-hexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

UV protection factors are, for example, organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances:

3-benzylidene camphor or 3-benzylidene norcamphor and derivatives thereof, for example 3-(4-methylbenzylidene)-camphor, as described in EP 0693471 B1;

4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester;

esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene);

esters of salicylic acid, preferably salicylic acid-2-ethylhexyl ester, salicylic acid4-isopropylbenzyl ester, salicylic acid homomenthyl ester;

derivatives of benzophenone, preferably 2-hydroxy4-methoxybenzo-phenone, 2-hydroxy4-methoxy4'-methylbenzophenone, 2,2'-dihydroxy-4-methoxybenzophenone;

esters of benzalmalonic acid, preferably 4-methoxybenzalmalonic acid di-2-ethylhexyl ester;

triazine derivatives such as, for example, 2,4,6-trianilino-(p-carbo-2'-ethyl-1'-hexyloxy)-1,3,5-triazine and Octyl Triazone, as described in EP 0 818 450 A1, or Dioctyl Butamido Triazine (Uvasorb® HEB);

propane-1,3-diones such as, for example, 1-(4-tert.butylphenyl)-3-(4'-methoxyphenyl)-propane-1,3-dione;

ketotricyclo(5.2.1)decane derivatives, as described in EP 0 694 521 B1.

Suitable water-soluble substances are 2-phenylbenzimidazole-5-sulfonic acid and alkali metal, alkaline earth metal, ammonium, alkylammonium, alkanolammonium and glucam-monium salts thereof;

sulfonic acid derivatives of benzophenones, preferably 2-hydroxy-4-methoxybenzophenone-5-sulfonic acid and salts thereof;

sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example 1-(4'-tert.butylphenyl)-3-(4'-methoxyphenyl)-propane-1,3-dione, 4-tert-butyl-4'-methoxydibenzoylmethane (Parsol 1789), 1-phenyl-3-(4'-isopropylphenyl)-propane-1,3-dione and the eneamine compounds described in DE 19712033 A1 (BASF). The UV-A and UV-B filters may of course also be used in the form of mixtures. Besides the soluble substances mentioned, insoluble pigments, i.e. finely dispersed metal oxides or salts, may also be used for this purpose. Examples of suitable metal oxides are, in particular, zinc oxide and titanium dioxide and also oxides of iron, zirconium, silicon, manganese, aluminium and cerium and mixtures thereof. Silicates (talcum), barium sulfate and zinc stearate may be used as salts. The oxides and salts are used in the form of the pigments for skin-care and skin-protecting emulsions. The particles should have an average diameter of less than 100 nm, preferably from 5 to 50 nm and more preferably from 15 to 30 nm. They may be spherical in shape although ellipsoidal particles or other non-spherical particles may also be used. The pigments may also be surface-treated, i.e. hydrophilicized or hydrophobicized. Typical examples are coated titanium dioxides such as, for example, Titandioxid T 805 (Degussa) or Eusolex® T2000 (Merck). Suitable hydrophobic coating materials are, above all, silicones and particularly trialkoxyoctyl silanes or simethicones. So-called micro- or nanopigments are preferably used in sun protection products. Micronized zinc oxide is preferably used. Other suitable UV filters can be found in P. Finkel's review in SÖFW-Journal 122, 543 (1996).

Besides the two above-mentioned groups of primary protection factors, secondary protection factors of the antioxidant type may also be used. Secondary sun protection factors of the antioxidant type interrupt the photochemical reaction chain which is initiated when UV rays penetrate into the skin. Typical examples of suitable antioxidants are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmole to μmole/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxy-butyrophenone, uric acid and derivatives thereof, mannose and derivatives thereof, Superoxid-Dismutase, zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Suitable dyes are any of the substances suitable and approved for cosmetic purposes as listed, for example, in the publication "Kosmetische Färbemittel" of the Farbstoffkommission der Deutschen Forschungs-gemeinschaft, Verlag Chemie, Weinheim, 1984, pages 81 to 106. These dyes are normally used in concentrations of 0.001 to 0.1% by weight, based on the mixture as a whole.

Treatment of the Tissue Papers With the Softening Preparations

The treatment of the tissue papers with the softening preparations may be carried out in known manner, the solution being applied to at least one side of the papers. Basically, any known method by which liquids or melts can be applied to more or less hard surfaces may be used for this purpose, including for example spraying, printing (for example flexographic printing), coating (gravure coating), extrusion and combinations of these methods. The papers/tissues may also be impregnated with the formulations. Application of the preparations is generally followed by a brief drying step. Processes for treating tissue papers with softening preparations are described in detail in the above-cited documents WO 95/35411 and WO 97/30216 to which reference is hereby specifically made.

EXAMPLES

To test performance properties, commercially available three-ply tissue papers with a recycled paper content of 95% and a weight of 18 g/m² were treated with PIT emulsions 1 to 10 according to the invention and with comparison preparations C1, C2, C3 and C4 (non-PIT) in quantities of 2.5 g/m². The papers were then dried for 30 minutes at 30° C., after which their softness was evaluated by a panel of six experienced testers on a scale of (+++) very soft to (+) soft. The sensorial feeling on touching the tissues was also evaluated. The results which represent the averages of three test series are set out in Tables 1a and 1b.

TABLE 1a

Softness of tissue papers using PIT emulsions

| performance | Composition | | | | | | |
|---|---|---|---|---|---|---|---|
| | 1 | 2 | 3 | 4 | 5 | C1 | C2 |
| Myristyl Myristate | — | — | — | 15.0 | — | — | 20.0 |
| Cetyl Palmitate | 10.0 | — | — | 1.0 | 12.0 | — | — |
| Cetearyl Isononanoate | — | 15.0 | — | — | — | — | — |
| Isostearyl Isononanoate | — | — | 20.0 | — | 3.0 | — | — |

TABLE 1a-continued

Softness of tissue papers using PIT emulsions

| performance | Composition | | | | | | |
|---|---|---|---|---|---|---|---|
| | 1 | 2 | 3 | 4 | 5 | C1 | C2 |
| Cetearyl Alcohol | 15.0 | 8.0 | 8.0 | 4.0 | 6.0 | 35.0 | 20.0 |
| Ceteareth-12 | 2.0 | 1.0 | 1.0 | 0.5 | — | 15.0 | — |
| Ceteareth-20 | 8.0 | 7.0 | 7.0 | 2.0 | 8.0 | — | 20.0 |
| Glyceryl Palmitate | — | 5.0 | 5.0 | — | 3.0 | — | — |
| Glyceryl Stearate | 5.0 | — | — | 5.0 | — | — | — |
| Dipalmitoylethyl Hydroxyethylmonium Methosulfate | — | 1.0 | — | 1.0 | — | — | — |
| Octyldodecanol | — | — | — | 2.0 | 3.0 | 15.0 | — |
| Calendula Oil | — | — | — | 5.0 | — | — | — |
| Aloe Vera | — | — | — | — | 10.0 | 1.0 | — |
| Glycerol | 3.0 | 3.0 | 2.5 | — | — | — | — |
| Water | | | | to 100 | | | |
| Softness | ++ | +++ | ++ | +++ | ++ | + | + |
| Sensorial evaluation | Moist | Moist | Moist | Dry | Dry | Flat | Flat |

TABLE 1b

Softness of tissue papers using PIT emulsions

| performance | Composition | | | | | | |
|---|---|---|---|---|---|---|---|
| | 6 | 7 | 8 | 9 | 10 | V3 | V4 |
| Myristyl Myristate | — | — | 15.0 | 15.0 | 15.0 | — | 15.0 |
| Cetyl Palmitate | 10.0 | 10.0 | 1.0 | 1.0 | 1.0 | 10.0 | 1.0 |
| Cetearyl Isononanoate | — | — | — | — | — | — | — |
| Isostearyl Isononanoate | — | — | — | — | — | — | — |
| Cetearyl Alcohol | 15.0 | 15.0 | 4.0 | 4.0 | 4.0 | 15.0 | 4.0 |
| Ceteareth-12 | 2.0 | 2.0 | 0.5 | 0.5 | 0.5 | 2.0 | 0.5 |
| Ceteareth-20 | 8.0 | 8.0 | 2.0 | 2.0 | 2.0 | 8.0 | 2.0 |
| Glyceryl Palmitate | — | — | — | — | — | — | — |
| Glyceryl Stearate | 5.0 | 5.0 | 5.0 | 5.0 | 5.0 | 5.0 | 5.0 |
| Dipalmitoylethyl Hydroxy-ethylmonium Methosulfate | — | — | 1.0 | 1.0 | 1.0 | — | 1.0 |
| Octyldodecanol | — | — | 8.0 | 8.0 | 8.0 | — | 8.0 |
| Calendula Oil | — | — | 5.0 | 5.0 | 5.0 | — | 5.0 |
| Chitosan[1] | 0.025 | 0.1 | 0.05 | 0.1 | — | — | — |
| Deoxyribonucleic acid[2] | — | 0.1 | — | 0.1 | 0.1 | — | — |
| Glycerol | 3.0 | 3.0 | — | — | — | 3.0 | — |
| Water | | | | to 100 | | | |
| Softness | ++ | +++ | ++ | +++ | ++ | + | + |
| Sensorial evaluation | Moist | Moist | Dry | Dry | Dry | Flat | Flat |

[1])Hydagen HCMF, Henkel KGaA
[2])Deoxyribonucleic acid: molecular weight ca. 70,000, purity (as determined by spectro-photometric measurement of absorption at 260 nm and 280 nm): at least 1.7

Several Formulation Examples are set out in Tables 2a and 2b below. (11–13 and 23–25) are formulations for baby cleaning wipes, (14,15,26,27) are o/w emulsions for soft creme wipes, (16–21, 28–33) are body-care emulsions and (22,34) are after-sun emulsions.

TABLE 2a

Formulation Examples

| Composition | 11 | 12 | 13 | 14 | 15 | 16 | 17 | 18 | 19 | 20 | 21 | 22 |
|---|---|---|---|---|---|---|---|---|---|---|---|---|
| Glyceryl Stearate (and) Ceteareth-20 (and) Ceteareth-12 (and) Cetearyl Alcohol (and) Cetyl Palmitate* | 9.5 | 13.5 | 11.4 | 8.5 | 13.1 | 10.4 | 12.4 | 9.2 | 8.3 | 14.0 | 13.5 | 15.5 |
| Ceteareth-20 | 2.4 | 0.4 | 1.1 | 2.9 | 0.4 | 2.9 | 0.5 | 2.4 | 3.1 | 0.2 | 0.3 | — |
| Cocoglycerides | 5.0 | — | 10.0 | — | 6.0 | — | 5.0 | — | — | — | 5.0 | 4.0 |
| C12/15 Benzoate | — | 5.0 | — | 4.0 | — | — | — | 4.0 | — | — | — | — |
| Dicaprylyl Carbonate | — | 6.0 | 6.0 | 4.0 | — | 5.0 | — | — | — | — | — | 3.0 |
| Dicaprylyl Ether | 5.0 | — | — | — | 4.0 | — | 6.0 | — | 5.0 | 8.0 | — | — |
| Dimethicone | 3.0 | 6.0 | — | — | 4.0 | — | 3.0 | 6.0 | — | 2.0 | 4.0 | 2.0 |
| Dioctyl Malate | — | — | — | 8.0 | — | — | | | | | | |
| Cyclomethicone | | | | | | | — | — | 3.0 | — | — | — |
| Cetearyl Isononanoate | 6.0 | — | — | 5.0 | — | — | — | 6.0 | — | — | 3.0 | 3.0 |
| Oleyl Erucate | — | 3.0 | — | — | 4.0 | 4.0 | — | 3.0 | 4.0 | — | 5.0 | — |
| Almond Oil | — | — | 2.0 | — | — | — | 4.0 | — | 1.0 | — | 4.0 | — |
| Octyldodecanol | — | 2.0 | — | — | — | 8.0 | — | — | — | 10.0 | — | 8.0 |
| Hexyldecanol (and) Hexyldecyl Laurate | — | — | — | 3.0 | 5.0 | — | — | — | 6.0 | — | — | — |
| Panthenol | | | | | | | 1.0 | | | | | |
| Bisabolol | | | | | | | 0.2 | | | | | |
| Tocopherol/tocopherol acetate | | | | | | | 1.0 | | | | | |
| Glycerin | | | | | | | 3.0 | | | | | |
| Water | | | | | | | to 100 | | | | | |

*) Emulgade ® SE, Henkel KGaA

TABLE 2b

Formulation Examples

| Composition | 23 | 24 | 25 | 26 | 27 | 28 | 29 | 30 | 31 | 32 | 33 | 34 |
|---|---|---|---|---|---|---|---|---|---|---|---|---|
| Glyceryl Stearate (and) Ceteareth-20 (and) Ceteareth-12 (and) Cetearyl Alcohol (and) Cetyl Palmitate* | 9.5 | 13.5 | 11.4 | 8.5 | 13.1 | 10.4 | 12.4 | 9.2 | 8.3 | 14.0 | 13.5 | 15.5 |
| Ceteareth-20 | 2.4 | 0.4 | 1.1 | 2.9 | 0.4 | 2.9 | 0.5 | 2.4 | 3.1 | 0.2 | 0.3 | — |
| Cocoglycerides | 5.0 | — | 10.0 | — | 6.0 | — | 5.0 | — | — | — | 5.0 | 4.0 |
| C12/15 Benzoate | — | 5.0 | — | 4.0 | — | — | — | 4.0 | — | — | — | — |
| Dicaprylyl Carbonate | — | 6.0 | 6.0 | 4.0 | — | 5.0 | — | — | — | — | — | 3.0 |
| Dacaprylyl Ether | 5.0 | — | — | — | 4.0 | — | 6.0 | — | 5.0 | 8.0 | — | — |
| Dimethicone | 3.0 | 6.0 | — | — | 4.0 | — | 3.0 | 6.0 | — | 2.0 | 4.0 | 2.0 |
| Dioctyl Malate | — | — | — | 8.0 | — | — | | | | | | |
| Cyclomethicone | | | | | | | — | — | 3.0 | — | — | — |
| Cetearyl Isononanoate | 6.0 | — | — | 5.0 | — | — | — | 6.0 | — | — | 3.0 | 3.0 |
| Oleyl Erucate | — | 3.0 | — | — | 4.0 | 4.0 | — | 3.0 | 4.0 | — | 5.0 | — |
| Almond Oil | — | — | 2.0 | — | — | — | 4.0 | — | 1.0 | — | 4.0 | — |
| Octyldodecanol | — | 2.0 | — | — | — | 8.0 | — | — | — | 10.0 | — | 8.0 |
| Chitosan[1] | 0.1 | 0.1 | 0.1 | 0.15 | 0.15 | 0.08 | 0.08 | 0.08 | 0.1 | 0.05 | 0.05 | 0.1 |
| Deoxyribonucleic acid[2] | 0.1 | 0.1 | 0.1 | 0.1 | 0.1 | 0.1 | 0.1 | 0.1 | 0.1 | 0.1 | 0.1 | 0.1 |
| Hexyldecanol (and) Hexyldecyl Laurate | — | — | — | 3.0 | 5.0 | — | — | — | 6.0 | — | — | — |
| Panthenol | | | | | | | 1.0 | | | | | |
| Bisabolol | | | | | | | 0.2 | | | | | |
| Tocopherol/Tocopherol Acetate | | | | | | | 1.0 | | | | | |
| Glycerin | | | | | | | 3.0 | | | | | |
| Water | | | | | | | to 100 | | | | | |

*) Emulgade ® SE, Henkel KGaA
[1]Hydagen HCMF, Henkel KGaA
[2]Deoxyribonucleic acid: molecular weight ca. 70,000, purity (as determined by spectro-photometric measurement of absorption at 260 nm and 280 nm): at least 1.7

What is claimed is:

1. A method of softening papers, nonwovens, tissues and/or cloths, said method comprising:
   (a) providing a substrate selected from the group consisting of papers, nonwovens, tissues and cloths;
   (b) providing a softening formulation comprising a phase inversion temperature emulsion comprising a non-aqueous phase comprised of (i) one or more $C_{8-22}$ fatty acid alkyl esters, (ii) one or more $C_{8-22}$ fatty alcohols, (iii) one or more $C_{8-22}$ alcohol polyglycol ethers, (iv) one or more $C_{8-22}$ fatty acid partial glycerides, and an aqueous phase; and
   (c) applying the softening formulation to the substrate.

2. The method according to claim 1, wherein the (i) one or more $C_{8-22}$ fatty acid alkyl esters corresponds to the general formula (I):

$$R^1CO\text{---}OR^2 \qquad (I)$$

wherein $R^1CO$ represents a linear or branched, saturated or unsaturated acyl group having from 8 to 22 carbon atoms and $R^2$ represents a linear or branched, alkyl or alkenyl group having from 6 to 22 carbon atoms.

3. The method according to claim 1, wherein the (i) one or more $C_{8-22}$ fatty acid alkyl esters comprises a wax ester having a total of 24 to 48 carbon atoms.

4. The method according to claim 1, wherein the (i) one or more $C_{8-22}$ fatty acid alkyl esters comprises an ester selected from the group consisting of myristyl myristate, cetearyl isononanoate, cetyl palmitate, cetyl stearate, stearyl palmitate, stearyl stearate, and mixtures thereof.

5. The method according to claim 1, wherein the (ii) one or more $C_{8-22}$ fatty alcohols corresponds to the general formula (II):

$$R^3OH \qquad (II)$$

wherein $R^3$ represents a linear or branched, alkyl or alkenyl group having from 8 to 22 carbon atoms.

6. The method according to claim 1, wherein the (ii) one or more $C_{8-22}$ fatty alcohols comprises an alcohol selected from the group consisting of cetyl alcohol, cetearyl alcohol, behenyl alcohol, 2-octyl dodecanol, and mixtures thereof.

7. The method according to claim 1, wherein the (iii) one or more $C_{8-22}$ alcohol polyglycol ethers corresponds to the general formula (III):

$$R^4O(CH_2CHR^5O)_nH \qquad (III)$$

wherein $R^4$ represents a linear or branched, alkyl or alkenyl group having from 8 to 22 carbon atoms, $R^5$ represents a hydrogen atom or a methyl group, and n is a number of from 1 to 50.

8. The method according to claim 7, wherein n is a number of from 5 to 40 and $R^5$ represents a hydrogen atom.

9. The method according to claim 1, wherein the (iii) one or more $C_{8-22}$ alcohol polyglycol ethers comprises an addition product of technical fatty alcohols having 16 to 18 carbon atoms with 10 to 20 moles of ethylene oxide.

10. The method according to claim 1, wherein the (iv) one or more $C_{8-22}$ fatty acid partial glycerides comprises a monoglyceride component corresponding to the general formula (IV):

$$HOCH_2CH(OH)CH_2OCOR^6 \qquad (IV)$$

wherein $R^6CO$ represents a linear or branched, saturated or unsaturated acyl group having from 8 to 22 carbon atoms.

11. The method according to claim 1, wherein the (iv) one or more $C_{8-22}$ fatty acid partial glycerides comprises a mixture of monoglycerides and diglycerides, wherein the mixture has a monoglyceride content of from 50 to 95% by weight based on total glycerides.

12. The method according to claim 1, wherein the (i) one or more $C_{8-22}$ fatty acid alkyl esters is present in an amount of from 1 to 70% by weight, the (ii) one or more $C_{8-22}$ fatty alcohols is present in an amount of from 1 to 40% by weight, the (iii) one or more $C_{8-22}$ alcohol polyglycol ethers is present in an amount of from 1 to 40% by weight, and the (iv) one or more $C_{8-22}$ fatty acid partial glycerides is present in an amount of from 1 to 40% by weight, wherein all percentages are based on the total weight of the non-aqueous phase and total 100%.

13. The method according to claim 12, wherein the non-aqueous phase of the softening formulation further comprises (v) one or more auxiliaries or additives, wherein the (v) one or more auxiliaries or additives is present in an amount of up to 70% by weight.

14. The method according to claim 1, wherein the non-aqueous phase is present in an amount of from 0.5 to 80% by weight, based on the total weight of the emulsion.

15. The method according to claim 14, wherein the (v) one or more auxiliaries or additives comprises a skin-care oil.

16. The method according to claim 14, wherein the (v) one or more auxiliaries or additives comprises a co-emulsifier.

17. The method according to claim 14, wherein the (v) one or more auxiliaries or additives comprises a substance selected from the group consisting of chitosans, (deoxy) ribonucleic acids, and mixtures thereof.

18. The method according to claim 14, wherein the (v) one or more auxiliaries or additives comprises a chitosan having an average molecular weight of from 800000 to 1200000 daltons.

19. The method according to claim 14, wherein the (v) one or more auxiliaries or additives comprises a chitosan present in an amount of from 0.001 to 2.5% by weight.

20. The method according to claim 19, wherein the non-aqueous phase of the softening formulation further comprises a (deoxy)ribonucleic acid.

21. The method according to claim 13, wherein the (v) one or more auxiliaries or additives comprises a (deoxy) ribonucleic acid present in an amount of from 0.001 to 2.5% by weight.

22. The method according to claim 19, wherein the non-aqueous phase of the softening formulation further comprises a chitosan.

23. A phase inversion temperature emulsion comprising a non-aqueous phase comprised of (a) one or more $C_{8-22}$ fatty acid alkyl esters, (b) one or more $C_{8-22}$ fatty alcohols, (c) one or more $C_{8-22}$ alcohol polyglycol ethers, (d) one or more $C_{8-22}$ fatty acid partial glycerides; and an aqueous phase.

24. An article comprising a substrate selected from the group consisting of papers, nonwovens, tissues and cloths, wherein the substrate has a surface area, at least a portion of the surface area coated with a softening formulation comprising a phase inversion temperature emulsion according to claim 23.

* * * * *